United States Patent [19]
Desai et al.

[11] Patent Number: 5,210,090
[45] Date of Patent: * May 11, 1993

[54] SUBSTITUTED N-BENZYLPIPERIDINE AMIDES AND CARDIAC REGULATORY COMPOSITIONS THEREOF

[75] Inventors: Bipinchandra N. Desai, Vernon Hills; Mark A. Russell, Skokie, both of Ill.

[73] Assignee: G. D. Searle & Co., Chicago, Ill.

[*] Notice: The portion of the term of this patent subsequent to Mar. 24, 2009 has been disclaimed.

[21] Appl. No.: 571,911

[22] Filed: Aug. 27, 1990

Related U.S. Application Data

[63] Continuation-in-part of Ser. No. 403,205, Sep. 5, 1989, Pat. No. 5,098,915.

[51] Int. Cl.$^5$ .................. A61K 31/445; C07D 401/12
[52] U.S. Cl. ..................... 514/320; 514/318; 546/193; 546/194; 546/196
[58] Field of Search ............... 514/318, 320; 546/193, 546/194, 196

[56] References Cited

U.S. PATENT DOCUMENTS

| | | | |
|---|---|---|---|
| 3,907,810 | 9/1975 | Cavalla et al. | 546/210 |
| 3,910,931 | 10/1975 | Cavalla et al. | 546/206 |
| 3,910,932 | 10/1975 | Cavalla et al. | 546/194 |
| 3,912,741 | 10/1975 | Cavalla et al. | 546/202 |
| 3,917,614 | 11/1975 | Cavalla et al. | 546/197 |
| 3,919,242 | 11/1975 | Cavalla et al. | 546/197 |
| 4,028,365 | 6/1977 | Cavalla et al. | 546/200 |
| 4,029,801 | 6/1977 | Cavalla et al. | 514/329 |
| 4,034,098 | 7/1977 | Archibald et al. | 514/329 |
| 4,045,444 | 8/1977 | Cavalla et al. | 546/197 |
| 4,046,767 | 9/1977 | Cavalla et al. | 546/197 |
| 4,061,640 | 12/1977 | Cavalla et al. | 546/175 |
| 4,138,492 | 2/1979 | Noverola et al. | 514/316 |
| 4,145,427 | 3/1979 | Langbein et al. | 514/329 |
| 4,277,501 | 7/1981 | Molley et al. | 514/654 |
| 4,289,781 | 9/1981 | Bengtsson et al. | 514/323 |
| 4,596,827 | 6/1986 | Molley et al. | 514/605 |

FOREIGN PATENT DOCUMENTS 1345872 2/1974 United Kingdom .

OTHER PUBLICATIONS

Effects of a Unique, New, Antihypertensive Agent (MJ-14712) on Arterial Blood Pressure and the Blood Pressure Response to Tilt (Orthostatic Hypotensive Potential) in Conscious Rats and Dogs. Flemming, J. S., et al., *Federation Proceedings*, vol. 43, p. 553 (1984).

*Primary Examiner*—Mary C. Lee
*Assistant Examiner*—Jacqueline Haley
*Attorney, Agent, or Firm*—Joy Ann Serauskas; Paul D. Matukaitis

[57] ABSTRACT

The invention relates to compound of the formula

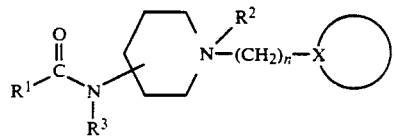

useful in regulating cardiac arrhythmias. This invention also relates to pharmaceutical compositions of the above-described compounds.

9 Claims, No Drawings

SUBSTITUTED N-BENZYLPIPERIDINE AMIDES AND CARDIAC REGULATORY COMPOSITIONS THEREOF

This application is a continuation-in-part of Ser. No. 07/403,205, filed Sep. 5, 1989, now U.S. Pat. No. 5,098,915.

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are Class III antiarrhythmic agents which, by effectively prolonging repolarization of a cardiac cell action potential, can be used effectively to treat certain cardiac arrhythmias. Antiarrhythmic drugs have been grouped together according to the pattern of electrophysiological effects that they produce and/or their presumed mechanisms of action. Thus, Class I antiarrhythmic agents are characterized by being sodium channel blockers, Class II antiarrhythmic agents are beta-adrenergic blockers, Class III antiarrhythmic agents prolong repolarization, and Class IV antiarrhythmic agents are calcium channel blockers.

Currently, there are very few Class III antiarrhythmic agents available for theraputic use. Among them is bretylium. Bretylium's usefulness is limited, however, and currently its theraputic use is reserved for life-threatening ventricular arrhythmias that are refractory to other therapy. Thus, bretylium's use is generally confined to intensive care units. It is an object of this invention to provide Class III antiarrhythmic agents of broader theraputic use than existing Class III antiarrhythmic agents.

SUMMARY OF THE INVENTION

The invention relates to compounds of the formula

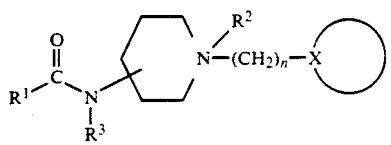

I the pharmaceutically acceptable nontoxic salts thereof or the hydrated forms thereof, wherein R' is substituted or unsubstituted benzofuranyl wherein said substituent is alkylsulfonamido wherein the alkyl portion is 1 to 4 carbon atoms with the proviso that R' is unsubstituted benzofuranyl only when

is alkysulfonamido substituented phenyl. n is an integer of from one to ten; $R^2$ is unsubstitutd or is alkyl of from one to ten carbon atoms or oxygen that is present as an N-oxide; $R^3$ is hydrogen, carboxyalkyl of from one to ten carbon atoms or alkoxycarbonylalkyl of from one to ten carbon atoms;

is hydrogen; pyridinyl; cycloalkyl of three to eight carbon atoms or hydroxy substituted cycloalkyl of three to eight carbon atoms; furanyl; or unsubstituted or substituted phenyl wherein said phenyl substituent is one or more of alkyl, halogen substituted alkyl of one to ten carbon atoms, alkoxy from one to ten carbon atoms, nitro, amine, mono or dialkylamine, acetyl amine, acetylamide, halogen, alkylsulfonamido wherein the alkyl portion is 1 to 4 carbon amine, mono or dialkylamine, acetyl amine, acetylamide, halogen, alkylsufonamido wherein the alkyl portion is 1 to 4 carbon atoms or alkoxy itself substituted by halogen substituted phenyl.

This embodiment is exemplified by the following compounds:
N-[1-[[4-[(methylsulfonyl)amino]phenyl]methyl]-4-piperidinyl]-2-benzofurancarboxamide
7-[(methylsulfonyl)amino]-N-[1-[[4[(methylsulfonyl)amino]phenyl]methyl]-4-piperidinyl]-2-benzofurancarboxamide
7-[(methylsulfonyl)amino]-N-[1-(phenylmethyl)-4-piperidinyl]2-benzofurancarboxamide The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

As used herein, the term "alkyl" shall mean straight or branched chain carbon-carbon linkages of from one to ten carbon atoms. "Alkenyl" shall have the same meaning, except that one or more double bonds may be present therein. "Alkynyl" shall have the same meaning, except that one or more triple bonds may be present therein "Alkoxy" shall include alkyl, alkenyl and alkynyl, as defined above, substituted by an epoxide oxygen "Aralkyl" shall include alkyl, alkenyl and alkynyl, as defined above, substituted by an aryl group, which is defined below.

"Aryl" shall mean phenyl.

"Halogen" shall include fluorine, chlorine, bromine or iodine.

The term "alkylsulfonamide" shall mean a radical of the formula

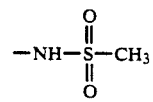

with the understanding that the alkyl portion of the radial may be expanded to 4 carbon atoms.

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydroiodic, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate, methaneperoxoate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail. $R^1$, $R^2$, $R^3$ and

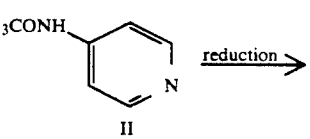

are as defined above. Y is any suitable leaving group, such as halogen, mesylate or tosylate COZ represents a suitable acylating agent such as a carboxylic acid chloride, a carboxylic acid activated as the mixed anydride, or the carboxylic ester activated by alkylaluminum reagents Scheme 1

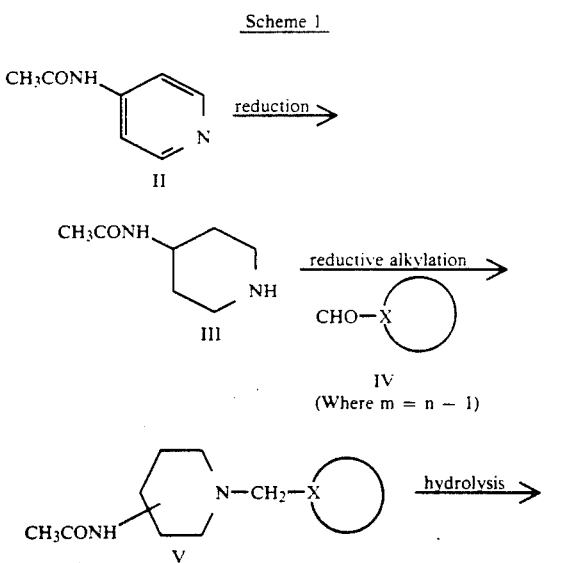

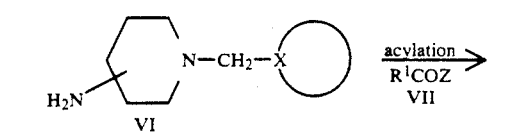

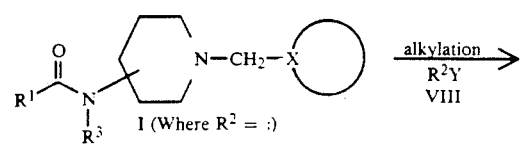

Scheme 1

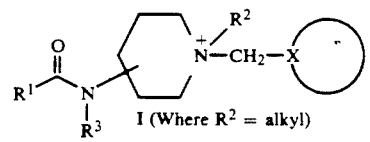

Scheme II

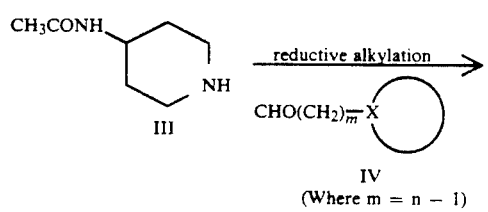

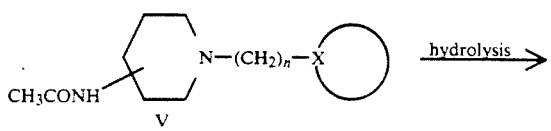

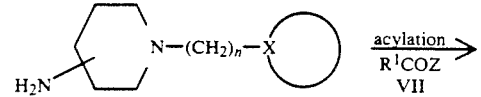

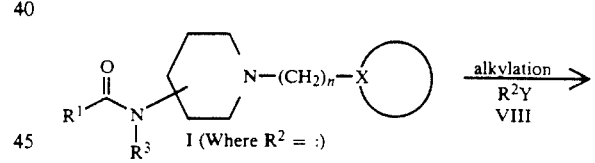

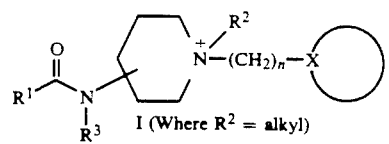

Reduction of 4-acetamidopyridine Formula II affords 4-acetamido-piperidine Formula III. A method for the preparation of 4-acetamidopiperidine III involves the reduction of 4-acylamino N-benzyl pyridinium compounds by alkali metal hydrides or catalytic hydrogenation of the aromatic ring with debenzylation as described in EP 1,537,867 (G. O. Weston) and EP 1,345,872 (J. L. Archibald and J. F. Cavalla) the disclosures of which are incorporated herein by reference. Preferred reduction conditions employ a ruthenium on carbon catalyst in a solvent such as alcohol, tetra hydrofuran, (THF), or acetic acid under an atmosphere of hydrogen. Subsequent reductive alkylation of the piperidine Formula III with aldehydes Formula IV provides the N-alkylated intermediates Formula V. Preferred conditions employ Pt/C catalyst in an inert solvent such as alcohol, THF, or acetic acid under an atmosphere of hydrogen. Alternative preferred conditions employ borane-pyridine complex as the reducing agent at room temperature in alcohol, acetic acid or methylene chloride. Hydrolysis of the amide bond of acetamides Formula V provides amine intermediates Formula VI. Although hydrolysis may be effected in acid or base, the preferred method employs hydrolysis in 1.2 M HCl at 100° C. Alternative preferred acylating conditions leading to amides I ($R^2$ = lone pair) employ COZ, which can be a carboxylic acid chloride, a carboxylic acid activated as the mixed anhydride, or the carboxylic ester activated by alkylaluminum reagents.

The intermediates Formula I are subsequently converted to the quaternary salts Formula I (where $R^2$ is not an unshared valence bond) by N-alkylating reagents $R^2X$ Formula VIII (where X is a suitable leaving group such as halogen, mesylate, or tosylate) in an inert solvent. Preferred alkylation conditions employ acetonitrile as the solvent at room temperature.

The compounds of the present invention can be administered in such oral dosage forms as tablets, capsules, pills, powders, granules, elixers, tinctures, suspensions, syrups and emulsions. Likewise, it can also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of arrhythmias of the heart. The dosage regimen utilizing the compound of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.1 mg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below will form the active ingredient that will typically be administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of tablets or capsules, the active drug component can be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components can be combined with any oral non-toxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like. The compounds of this invention can also be administered by intravenous route in doses ranging from 0.1 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrythmic activity useful in the treatment of various cardiac arrhythmias. The test procedures employed to measure this activity of the compounds of the present invention are described below.

EXAMPLE 1

Guinea pigs, of either sex weighing between 200–350 g, are acutely sacrificed and the right ventricular papillary muscle is isolated. A sample of a given test compound is added using an in vitro tissue bath. Concentrations used are generally $3 \times 10^{-5}$M, but may also be as low as $3 \times 10^{-7}$M. Changes in refractory period are measured before and after adding 1 concentration (usually $3 \times 10^{-5}$M, as noted above) of a test compound to the bath. One hour is allowed for drug equilibration. A compound is considered active (Class III) if an increase in ventricular refractory period is 25 msec or more (at $3 \times 10^{-5}$M).

| Compound | Results Concentration (M) | Change (msec) |
| --- | --- | --- |
| $H_2O$ | — | 8 |
| Disopyramide | $3 \times 10^{-5}$ | 20 |
| Clofinium | $3 \times 10^{-5}$ | 24 |
| Sotalol | $3 \times 10^{-5}$ | 35 |
| Example 9 | $3 \times 10^{-5}$ | 55 |
| Example 10 | $3 \times 10^{-5}$ | 50 |
| Example 11 | $3 \times 10^{-5}$ | 30 |
| Example 12 | $1 \times 10^{-6}$ | 20 |
| Example 13 | $3 \times 10^{-5}$ | 40 |
| Example 14 | $1 \times 10^{-6}$ | 15 |
| Example 15 | $3 \times 10^{-5}$ | 40 |
| Example 16 | $1 \times 10^{-6}$ | 30 |
| Example 17 | $3 \times 10^{-5}$ | 30 |
| Example 18 | $3 \times 10^{-5}$ | 55 |
| Example 19 | $1 \times 10^{-6}$ | 25 |
| Example 20 | $1 \times 10^{-6}$ | 40 |
| Example 21 | $3 \times 10^{-5}$ | 190 |
| Example 22 | $3 \times 10^{-5}$ | 95 |
| Example 23 | $3 \times 10^{-5}$ | 35 |
| Example 24 | $3 \times 10^{-5}$ | 60 |
| Example 25 | $3 \times 10^{-5}$ | 60 |

-continued

| Compound | Results Concentration (M) | Change (msec) |
| --- | --- | --- |
| Example 26 | $3 \times 10^{-5}$ | 90 |
| Example 29 | $3 \times 10^{-6}$ | 60 |
| Example 87 | $3 \times 10^{-6}$ | 55 |
| Example 30 | $3 \times 10^{-6}$ | 80 |
| Example 36 | $3 \times 10^{-6}$ | 55 |
| Example 37 | $3 \times 10^{-5}$ | 35 |
| Example 39 | $3 \times 10^{-5}$ | 155 |
| Example 40 | $3 \times 10^{-5}$ | 125 |
| Example 41 | $3 \times 10^{-6}$ | 70 |
| Example 42 | $3 \times 10^{-6}$ | 60 |
| Example 44 | $3 \times 10^{-6}$ | 40 |
| Example 46 | $3 \times 10^{-6}$ | 95 |
| Example 51 | $3 \times 10^{-6}$ | 75 |
| Example 53 | $3 \times 10^{-6}$ | 50 |
| Example 58 | $3 \times 10^{-6}$ | 60 |
| Example 59 | $3 \times 10^{-6}$ | 35 |
| Example 60 | $3 \times 10^{-6}$ | 25 |
| Example 64 | $3 \times 10^{-5}$ | 85 |
| Example 66 | $3 \times 10^{-5}$ | 45 |
| Example 69 | $3 \times 10^{-5}$ | 25 |
| Example 70 | $3 \times 10^{-5}$ | 40 |
| Example 72 | $3 \times 10^{-5}$ | 50 |
| Example 75 | $3 \times 10^{-5}$ | 60 |
| Example 77 | $1 \times 10^{-6}$ | 60 |
| Example 78 | $3 \times 10^{-6}$ | 50 |
| Example 80 | $3 \times 10^{-5}$ | 115 |
| Example 82 | $3 \times 10^{-6}$ | 55 |
| Example 90 | $3 \times 10^{-6}$ | 50 |
| Example 91 | $3 \times 10^{-6}$ | 65 |
| Example 92 | $3 \times 10^{-5}$ | 55 |

The following non-limiting examples further illustrate details for the preparation of the compounds of the present invention. Those skilled in the art will readily understand that known variations of the conditions and processes of the following preparative procedures can be used to prepare these compounds. All termperatures are degrees Celsius unless otherwise noted. Melting points were determined on a Thomas-Hoover Unimelt Capillary Apparatus and are not corrected. Unless otherwise noted, I.R. and NMR spectra were consistent with the assigned structure.

EXAMPLE 2

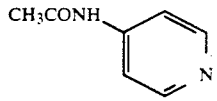

Preparation of 4-acetamidopyridine acetate II

4-Aminopyridine (101.28 g) and acetic anhyride (110 g) were mixed neat and heated at 100° C. for ½ h. The solidified reaction mixture was triturated with acetone, filtered off, and washed with ether to afford 186.48 g of II as a white solid in two crops. Anal. calcd for $C_9H_{12}N_2O_3$: C, 55.09; H, 6.16; N, 14.26. Found: C, 55.04; H, 5.96; N, 15.22.

EXAMPLE 3

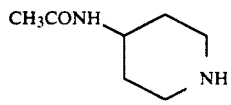

Preparation of 4-acetamidopiperidine acetate III

A solution of the product of Example 2 (75 g) in 750 mL acetic acid was reduced over $PtO_2$ catalyst at 60 psi hydrogen atmosphere at 60° C. for 7 hours. The solution was filtered, concentrated and triturated with ether to afford the title compound quantitatively as a white solid which was used directly in subsequent reactions.

EXAMPLE 4

Preparation of 1-(4-methoxyphenyl)methyl-4-acetamido-piperidine

A mixture of 10 g amine acetate from Example 3 and 13.48 g 4-methoxy benzaldehyde was hydrogenated in 100 mL ethanol over a Pt/C catalyst at room temperature for 3 hours. The reaction mixture ws filtered and concentrated to give 74.0 g of the acetate salt of the title compound as a white solid which was hydrolyzed directly as described in Example 4. (An alternative reductive amination procedure is described in Example 5). Conversion of a sample to the free base using aqueous base and ethyl acetate extraction provided a white solid after solvent evaporation and trituration with ether: mp 140°-142° C; Anal. calcd for $C_{15}H_{22}N_2O_2$: C, 68.67; H, 8.45; N, 10.68. Found: C, 65.26; H, 8.60; N, 10.77.

EXAMPLE 5

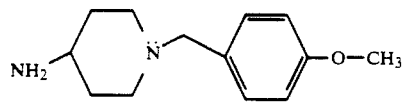

Preparation of 1-(4-methoxyphenyl)methyl-4-amino piperidine

A) A solution of 50 g of the product of Example 4 was dissolved in 500 mL of 1.2N HCl and heated at 100° C. for 8 h. The solution was made alkaline with 50% aq. NaOH and extracted three times with ether. The combined organic layers were washed with water and saturated brine, dried over sodium sulfate, and concentrated to give the title compound as 28 g of clear oil which was used without further purification.

B) (Alternative general reductive alkylation procedure) A solution of 50 mmol amine acetate (product of Example 3) and 100 mmol of 4-methoxybenzaldehyde in 125 mL methylene chloride and 15 mL acetic acid was treated with 50 mmol of borane-pyridine complex and allowed to stir at room temperature overnight. The removal of volatiles by rotary evaporation afforded the acetamide of Example 4 as an oil which was dissolved in 300 mL of 1.2N HCl and heated overnight on a steam bath. The cooled reaction mixture was extracted once with a 50 mL portion of ethyl acetate which was discarded. The aqueous layer was made basic with aq. NaOH and extracted three times with 50 mL ether. The combined layers were washed with water and dried over sodium sulfate. Solvent removal afforded the title compound as a crude oil (yield typically 60-70% for two steps) which was used directly without further purification.

EXAMPLE 6

General acylation procedures

A) 10 mmol of the amine of Example 5 is dissolved in a mixture of 25 mL chloroform and 11 mmol of triethylamine cooled to 0° C. A solution of 11 mmol of the acyl chloride neat or dissolved in 25 mL chloroform is added dropwise and the reaction mixture is allowed to stir for 1 h. Volatiles are removed in vacuo and the residue is partitioned between dilute aqueous base and ethyl acetate. Drying of the ethyl acetate extract and evaporation leads to the crude product which is optionally purified by flash chromatography on silica gel using 92.5:7:0.5 chloroform: ethanol: ammonium hydroxide and crystallized from ethyl acetate/hexane or converted to the HCl salt using dioxane/HCl followed by recrystallization from methanol/ether.

B) A stirred solution of 10 mmol acylating acid in 25 mL chloroform is treated with 10 mmol of triethylamine followed by 10 mmol of isobutyl chloroformate. After 10 minutes at ambient temperature the amine of Example 5 was added and the reaction is allowed to stir for ½ h. The reaction mixture is washed with 10% NaOH solution and the organic layer is dried and evaporated to give a residue which is optionally purified by flash chromatography on silica gel using 92.5:7:0.5 chloroform:ethanol:ammonium hydroxide recrystallized from ethyl acetate converted to the HCl salt using dioxane/HCl followed by recrystallization from methanol/ether.

EXAMPLE 7

Preparation of quaternary salt

A solution of 200 mg of the amide of Example 6 in 5 mL acetone was treated with 4 drops of iodomethane. The reaction mixture was stirred for 18 h and the white crystalline precipitate was filtered off to afford 206 mg of white solid which was recrystallized from acetonitrile to give 128 mg of quaternary iodide as fluffy white needles, mp 236°-237° C.

EXAMPLE 8

Preparation of N-oxide

A solution of 0.50 g of the amide of Example 6 in 10 mL $CH_2Cl_2$ was treated with 300 mg of m-chloroperoxybenzoic acid at 0° C. After 1 h the solution was washed consecutively with 10 mL 1N NaOH, water, and sat'd. brine. The solution was dried over sodium sulfate and concentrated to afford 0.51 g of white solid which was recrystallized from $CH_2Cl_2$/ethyl acetate to give 0.33 g of an N-oxide as a white powder, mp 200.5°-202.5° C.

EXAMPLE 9 through 91

Using the procedures of Examples 2 through 8 and making the appropriate substitutions at positions $R_1$, $R_2$, $R_3$, and

the following products were obtained as presented in Table I below. Table I specifies the moiety at $R_1$, $R_2$, $R_3$ and

the number of methylenes represented by n, the compound's melting point range in degrees Celsius (where available) and the compound's elemental analysis.

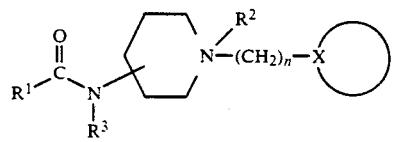

All piperidinyls are 4-piperidinyl unless otherwise noted.

| Example | R¹ | R² | R³ | X | n | mp, deg. C. | Analysis |
|---|---|---|---|---|---|---|---|
| 9 | 4-pyridyl | | H | phenyl | 1 | | $C_{18}H_{21}N_3O$ |
| 10 | 3-pyridyl | | H | phenyl | 1 | | $C_{18}H_{21}N_3O$ |
| 11 | 2-pyridyl | | H | phenyl | 1 | | $C_{18}H_{21}N_3O$ |
| 12 | cyclohexyl | | H | 4-chlorobenzyloxy-4-phenyl | 1 | | $C_{26}H_{33}ClN_2O_2$ |
| 13 | cyclohexyl | | H | phenyl | 1 | 155–157 | $C_{19}H_{28}N_2O$ |
| 14 | anilino (PhNH–) | | H | phenyl | 1 | 168–169.5 | $C_{19}H_{23}N_3O$ |
| 15 | 2-furyl | | H | phenyl | 1 | 155.5–158 | $C_{17}H_{20}N_2O_2$ |
| 16 | cyclohexyl | | H | 4-methoxyphenyl | 1 | 170–171 | $C_{20}H_{30}N_2O_2$ |

-continued

| Example | R¹ | R² | R³ | X | n | mp, deg. C. | Analysis |
|---|---|---|---|---|---|---|---|
| 17 | —CH₃ | | H | 4-CH₃O-C₆H₄ | 1 | 137-140 | $C_{15}H_{22}N_2O_2$ |
| 18 | 2-furyl | | H | 4-CH₃O-C₆H₄ | 1 | 136-137 | $C_{18}H_{22}N_2O_3$ |
| 19 | cyclopropylmethyl-phenyl | | H | 4-CH₃O-C₆H₄ | 1 | 142-143 | $C_{21}H_{28}N_2O_2$ |
| 20 | cinnamyl | | H | 4-CH₃O-C₆H₄ | 1 | 135-137 | $C_{22}H_{26}N_2O_2$ |
| 21 | benzofuranyl-methyl | | H | 4-CH₃O-C₆H₄ | 1 | 136-138 | $C_{22}H_{24}N_2O_3$ |
| 22 | pyridyl-methyl | | H | 4-CH₃O-C₆H₄ | 1 | | $C_{19}H_{23}N_3O_2$ |
| 23 | thienyl-methyl | | H | 4-CH₃O-C₆H₄ | 1 | 161-162 | $C_{18}H_{22}N_2O_2S$ |
| 24 | coumarinyl-methyl | | H | 4-CH₃O-C₆H₄ | 1 | 200-202 | $C_{23}H_{24}N_2O_4$ |

-continued

| Example | R¹ | R² | R³ | X | n | mp. deg. C. | Analysis |
|---|---|---|---|---|---|---|---|
| 25 | imidazole-vinyl | | H | 4-methoxyphenyl | 1 | 210-211 | $C_{19}H_{24}N_2O_2$ |
| 26 | imidazole-N-carboxylate (isobutyl) vinyl | | H | 4-methoxyphenyl | 1 | 134-137 | $C_{24}H_{32}N_2O_4$ |
| 27 | $CH_3$ | | H | 4-methoxyphenyl | 2 | 162-164 | $C_{16}H_{24}N_2O_2$ |
| 28 | 2-methylfuran | | H | 4-methoxyphenyl | 1 | 178.5-179.5 | $C_{18}H_{22}N_2O_2$ |
| 29 | 3-methylbenzofuran | | H | 4-methoxyphenyl | 1 | 140-141 | $C_{22}H_{24}N_2O_3$ |
| 30 | dimethyl-indanyl | | H | 4-methoxyphenyl | 1 | 135-137 | $C_{23}H_{28}N_2O_2$ |
| 31 | styryl | | H | 4-propoxyphenyl | 1 | 156-158 | $C_{24}H_{30}N_2O_2$ |

-continued

| Example | R¹ | R² | R³ | X | n | mp. deg. C. | Analysis |
|---|---|---|---|---|---|---|---|
| 32 | 2-methylfuran-5-yl | | H | 4-(O-(CH₂)₂CH₃)-phenyl | 1 | 122–124 | $C_{20}H_{26}N_2O_3$ |
| 33 | 2-methylbenzofuran-3-yl | | H | 4-(O-(CH₂)₂CH₃)-phenyl | 1 | 132–134 | $C_{24}H_{28}N_2O_3$ |
| 34 | 5-chloro-2-methylbenzofuran-3-yl | | H | 4-OCH₃-phenyl | 1 | 148–149 | $C_{22}H_{23}ClN_2O_3$ |
| 35 | 3-methyl-2-methylbenzofuran-3-yl | | H | 4-OCH₃-phenyl | 1 | 156–158 | $C_{23}H_{26}N_2O_2$ |
| 36 | 7-methoxy-2-methylbenzofuran-3-yl | | H | 4-OCH₃-phenyl | 1 | 140–142 | $C_{23}H_{26}N_2O_4 \cdot HCl$ |
| 37 | 6,7-dimethoxy-2-methylbenzofuran-3-yl | | H | 4-OCH₃-phenyl | 1 | 147–148 | $C_{24}H_{28}N_2O_5$ |
| 38 | 7-chloro-2-methylbenzofuran-3-yl | | H | 4-OCH₃-phenyl | 1 | 126–128 | $C_{22}H_{23}ClN_2O_3$ |

-continued
| Example | R² | R³ | X | n | mp. deg. C. | Analysis |
|---------|----|----|---|---|-------------|----------|
| 39 | 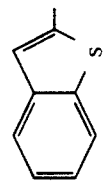 | H | 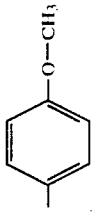 | 1 | 158-160 | $C_{22}H_{24}N_2O_2S$ |
| 40 | 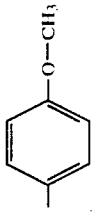 | H | 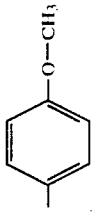 | 1 | 270-272 | $C_{23}H_{24}N_2O_4 \cdot HCl$ |
| 41 | 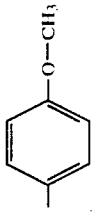 | H | 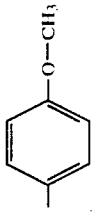 | 1 | oil | $C_{22}H_{25}N_2O_2 \cdot HCl$ |
| 42 | 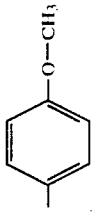 | H | 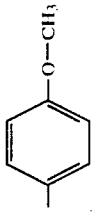 | 1 | 146-148 | $C_{23}H_{28}N_2O_3$ |
| 43 | 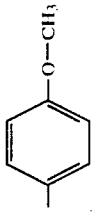 | H | | 1 | 147-149 | $C_{23}H_{28}N_2O_3$ |
| 44 | | H | | 1 | 145-147 | $C_{20}H_{25}N_3O_2$ |
| 45 | | H | | 1 | 150-152 | $C_{21}H_{25}N_3O_2$ |
| 46 | | H | | 1 | 142-144 | $C_{23}H_{26}N_2O_3$ |

-continued

| Example | R¹ | R² | R³ | X | n | mp. deg. C. | Analysis |
|---|---|---|---|---|---|---|---|
| 47 | phenyl-CH₂CH₂– | | H | 4-methoxyphenyl | 1 | 131–133 | $C_{22}H_{28}N_2O_2$ |
| 48 | 2-methoxyphenyl-CH=CH– | | H | 4-methoxyphenyl | 1 | 141–143 | $C_{23}H_{28}N_2O_2$ |
| 49 | phenyl-CH₂CH₂CH₂– | | H | 4-methoxyphenyl | 1 | 125–127 | $C_{23}H_{30}N_2O_2 \cdot HCl$ |
| 50 | 2-methoxyphenyl-CH=CH– | | H | 4-methoxyphenyl | 1 | 92–96 | $C_{23}H_{28}N_2O_2 \cdot HCl$ |
| 51 | 2,3-dihydrobenzofuran-2-yl (±) | | H | 4-methoxyphenyl | 1 | 134.5–135 | $C_{22}H_{26}N_2O_3$ |
| 52 | phenyl-CH₂– | | H | 4-methoxyphenyl | 1 | — | $C_{21}H_{26}N_2O_2$ |
| 53 | 5-nitro-2-methylbenzofuran-3-yl | | H | 4-methoxyphenyl | 1 | 190–192 | $C_{22}H_{23}N_3O_5$ |
| 54 | 4-nitrophenyl-CH=CH– | | H | 4-methoxyphenyl | 1 | 197–199 | $C_{22}H_{25}N_3O_4$ |

-continued

| Example | R¹ | R² | R³ | X | n | mp, deg. C. | Analysis |
|---|---|---|---|---|---|---|---|
| 55 | CH=CH-CH₃ | | H | 4-OCH₃-C₆H₄ | 1 | | C₁₇H₂₄N₂O₂ |
| 56 | 2,6-dichlorobenzylidene-propyl | | H | 4-OCH₃-C₆H₄ | 1 | 210-212 | C₂₂H₂₄Cl₂N₂O₂ |
| 57 | tetrahydronaphthyl (−) | | H | 4-OCH₃-C₆H₄ | 1 | 142-143 | C₂₄H₃₀N₂O₂ |
| 58 | 5-bromo-2-methylfuryl-vinyl | | H | 4-OCH₃-C₆H₄ | 1 | 133-135 | C₁₈H₂₁BrN₂O₃ |
| 59 | 2-methylbenzofuranyl | | H | C₆H₅ | 1 | 155-157 | C₂₁H₂₂N₂O₃ |
| 60 | 4-(methylsulfonylamino)styryl | | H | 4-OCH₃-C₆H₄ | 1 | 215-218 | C₂₃H₂₉N₃O₄S |
| 61 | CH₃ | | H | 4-NO₂-C₆H₄ | 1 | 143-144 | C₁₄H₁₉N₃O₃ |
| 62 | 2-methylbenzofuranyl | | H | 4-NO₂-C₆H₄ | 1 | 155-157 | C₂₁H₂₁N₃O₄ |

-continued

| Example | R¹ | R² | R³ | X | n | mp, deg. C. | Analysis |
|---|---|---|---|---|---|---|---|
| 63 | CH₃ |  | H | 4-Cl-phenyl | 1 | 162-164 | $C_{14}H_{19}ClN_2O$ |
| 64 | 2-methyl-benzofuran-3-yl |  | H | 4-Cl-phenyl | 1 | 137-139 | $C_{21}H_{21}ClN_2O_2$ |
| 65 | 2-methyl-tetrahydronaphthyl (+) |  | H | 4-OCH₃-phenyl | 1 | 157-159 | $C_{24}H_{30}N_2O_2$ |
| 66 | 2-methyl-benzofuran-3-yl |  | H | 4-OCH₃-phenyl | 1 | 236-237 | $C_{23}H_{26}N_2O_3 \cdot HI$ |
| 67 | 2-methyl-benzofuran-3-yl | CH₃ | H | cyclohexyl | 1 | 184-185.5 | $C_{21}H_{28}N_2O_2$ |
| 68 | CH₃ |  | H | 4-pyridyl | 1 | 163-164.5 | $C_{13}H_{19}N_3O$ |
| 69 | CH₃ |  | H | 4-OCH₃-phenyl (3-piperidyl) | 1 | 103-105 | $C_{15}H_{22}N_2O_2$ |
| 70 | benzofuran-3-yl |  | H | 4-OCH₃-phenyl (3-piperidyl) | 1 | 114-115 | $C_{22}H_{24}N_2O_3$ |

-continued

| Example | R¹ | R² | R³ | X | n | mp. deg. C. | Analysis |
|---------|----|----|----|---|---|-------------|----------|
| 71 | $CH_3$ | | H | 3-methoxyphenyl | 1 | | $C_{15}H_{22}N_2O_2$ |
| 72 | benzofuran-3-yl | O | H | 4-methoxyphenyl | 1 | 200.5–202.5 | $C_{22}H_{24}N_2O_4$ |
| 73 | $CH_3$ | | H | H | 1 | | $C_{15}H_{18}N_2O_2$ |
| 74 | benzofuran-3-yl | | H | 4-(acetylamino)phenyl | 1 | 145–147 | $C_{16}H_{23}N_3O_2 \cdot CHOOOH$ |
| 75 | benzofuran-3-yl | | H | 4-(acetylamino)phenyl | 1 | 230–232 | $C_{23}H_{25}N_3O_3$ |
| 76 | benzofuran-3-yl | | H | 3-methoxyphenyl | 1 | | $C_{22}H_{25}ClN_2O_3$ |
| 77 | benzofuran-3-yl | | H | 2,4-dimethoxyphenyl | 1 | | $C_{23}H_{26}N_2O_4$ |

-continued

| Example | R¹ | R² | R³ | X | n | mp. deg. C. | Analysis |
|---|---|---|---|---|---|---|---|
| 79 | benzofuran-2-yl | | H | 4-N(CH₃)₂-phenyl | 1 | | $C_{23}H_{27}N_3O_2 \cdot 2(HCl)$ |
| 80 | 5-nitrobenzofuran-2-yl | | H | 4-OCH₃-phenyl | 1 | 189–190 | $C_{22}H_{23}N_3O_5$ |
| 81 | 5-aminobenzofuran-2-yl | | H | 4-OCH₃-phenyl | 1 | 98–100 | $C_{22}H_{27}N_3O_3 \cdot 2(HCl)$ |
| 82 | CH₃ | | H | phenyl | 1 (substituted by CO₂CH₂CH₃) | | $C_{17}H_{24}N_2O_3$ |
| 83 | benzofuran-2-yl | | —CH₂CO₂CH₂CH₃ | 4-OCH₃-phenyl | 1 | | $C_{26}H_{31}ClN_2O_5$ |
| 84 | benzofuran-2-yl | | —CH₂CO₂H | 4-OCH₃-phenyl | 1 | | $C_{24}H_{26}N_2O_5$ |
| 85 | tetrahydronaphthalen-2-yl (±) | | H | 4-OCH₃-phenyl | 1 | 152–153 | $C_{24}H_{30}N_2O_2$ |
| 86 | benzofuran-2-yl | | H | 4-OH-phenyl | 1 | 198–200 | $C_{21}H_{22}N_2O_3$ |

-continued

| Example | R¹ | R² | R³ | X | n | mp, deg. C. | Analysis |
|---|---|---|---|---|---|---|---|
| 86 | CH₃ | | H | 3-furyl | 1 | | C₁₂H₁₈N₂O₂ |
| 87 | 1-indanyl | | H | 4-methoxyphenyl | 1 | | C₂₃H₂₈N₂O₂ |
| 88 | phenyl | | H | 4-trifluoromethylphenyl | 1 | | C₂₀H₂₂N₂OF₃ |
| 89 | 2-methoxyphenyl | | H | 4-methoxyphenyl | 1 | | C₂₁H₂₇N₂O₃ |
| 90 | 7-nitro-2-methylbenzofuran-3-yl | H | H | 4-nitrophenyl | 1 | | C₂₁H₂₀N₄O₆ |
| 91 | 7-nitro-2-methylbenzofuran-3-yl | H | H | phenyl | 1 | | C₂₁H₂₁N₃O₄ |

EXAMPLE 92

Preparation of

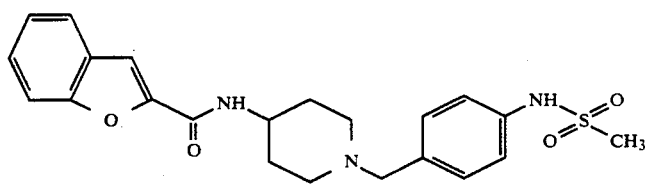

N-[1-[[4-[(methylsulfonyl)amino]phenyl]methyl]-4-piperidinyl]-2-benzofurancarboxamide To a solution of Example 62 (1.2 g, 3.16 mmol) in ethanol (10 ml) and concentrated hydrochloric acid (10 ml), tin (11) chloride monohydrate (2.15 g, 9.5 mmol) was added. The resulting solution was heated (steam bath) for 30 min., cooled to room temperature and adjusted to pH 10.0 by careful addition of 1N potassium hydroxide solution. The resulting aqueous solution was extracted with methylene chloride. The organic extracts were separated; dried ($Na_2SO_4$) and evaporated to afford the crude amino derivative (820 mg).

To a stirred solution of the amino derivative (349 mg) in methylene chloride (10 ml) at $-78°$, triethylamine (0.5 ml) and methane sulphonyl chloride (0.1 ml) was added. The reaction mixture was allowed to attain room temperature and stirred for a further 15 mins. The reaction mixture was quenched with saturated $NaHCO_3$ solution and extracted with methylene chloride. The organic extracts were separated, dried ($Na_2SO_4$) and evaporated in vacuo to afford the claimed compound (340 mg) recrystallized from ethylacetate, methylene chloride, methanol).

Anal. calcd for $C_{22}H_{25}N_3O_4S$, 0.6 $CH_2CL_2$; C 56.73, H, 5.52, N, 8.78. Found C, 56.39, H, 5.45, N, 80.71.

EXAMPLE 93

Preparation of

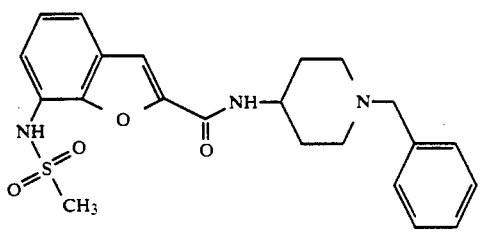

7-[(methylsulfonyl)amino]-N-[1-(phenylmethyl)-4-piperidinyl]-2-benzofurancarboxamide Following the procedure of Example 92 the final product of Example 91 was converted to the title compound.

Anal. calcd for $C_{22}H_{25}N_3O_4S$, C, 61.81, H, 5.89, N, 9.83. Found, C, 62.08, H, 5.89, N, 9.91.

EXAMPLE 94

Preparation of

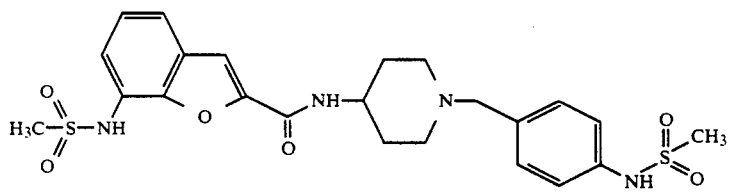

7-[(methylsulfonyl)amino]-N-[1-[[4-[(methylsulfonyl)amino]phenyl]methyl]-4-piperidinyl]-2-benzofurancarboxamide Following the procedure of Example 92 the final product of Example 90 was converted to the title compound.

Cald for $C_{22}H_{25}N_3O_4S$, $1H_2O$, ¼ EtOAc, C, 51.42, H, 5.75, N, 9.99, S, 11.44. Found C, 51.57, H, 5.50, N, 9.63, S, 11.52.

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations for differences in the results are contemplated in accordance with the objects and practices of the present invention. It is intended, therefore, that the invention be limited only by the scope of the claims which follow, and that such claims be interpreted as broadly as is reasonable.

What we claim is:

1. A compound of the formula

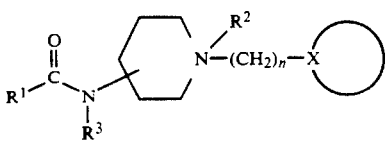

the pharmaceutically acceptable nontoxic salts thereof or the hydrated forms thereof, wherein $R^1$ is substituted or unsubstituted benzofuranyl wherein said substituent is alkylsulfonamido wherein the alkyl portion is 1 to 4 carbon atoms with the proviso that $R^1$ is unsubstituted benzofuranyl only when

is alkyl sulfonamido substituted phenyl;

n is an integer of from one to ten;

$R^2$ is unsubstituted or is alkyl of from one to ten carbon atoms or oxygen that is present as an N-oxide;

$R^3$ is hydrogen, carboxyalkyl of from one to ten carbon atoms or alkoxycarbonylalkyl of from one to ten carbon atoms;

is hydrogen; pyridinyl; cycloalkyl of three to eight carbon atoms or hydroxy substituted cycloalkyl of three to eight carbon atoms; furanyl; or unsubstituted or substituted phenyl wherein said phenyl substituent is one or more of alkyl, halogen substituted alkyl of one to ten carbon atoms, alkoxy from one to ten carbon atoms, nitro, amine, mono or dialkylamine, acetyl amine, acetylamide, halogen, alkylsulfonamido wherein the alkyl portion is 1 to 4 carbon atoms, alkoxy itself substituted by halogen substituted phenyl.

2. A compound according to claim 1 of the formula

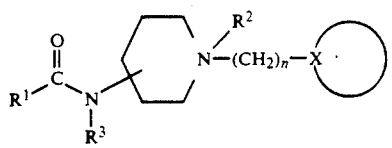

the pharmaceutically acceptable nontoxic salts thereof or the hydrated forms thereof, wherein $R^1$ is substituted or unsubstituted benzofuranyl wherein said substituent is alkylsulfonamido wherein the alkyl portion is 1 to 4 carbon atoms with the proviso that $R^1$ is unsubstituted benzofuranyl only when

is alkylsulfonamido substituented phenyl;

n is an integer of from one to ten;

$R^2$ is unsubstituted or is alkyl of from one to ten carbon atoms; $R^3$ is hydrogen;

is hydrogen; unsubstituted or substituted phenyl wherein said phenyl substituent is one or more of alkyl, halogen substituted alkyl of one to ten carbon atoms, alkoxy from one to ten carbon atoms, nitro, amine, mono or dialkylamine, acetyl amine, acetylamide, halogen, alkylsulfonamido wherein the alkyl portion is 1 to 4 carbon atoms, alkoxy itself substituted by halogen substituted phenyl.

3. A compound according to claim 1 which is N-[1-[[4-[(methylsulfonyl)amino]phenyl]methyl]-4-piperidinyl]-2-benzofurancarboxamide.

4. A compound according to claim 1 which is 7-[(methylsulfonyl)amino]-N-[1-[[4-[(methylsulfonyl) amino]phenyl]methyl]-4-piperidinyl]-2-benzofurancarboxamide.

5. A compound according to claim 1 which is 7-[(methylsulfonyl)amino]-N-[1-(phenylmethyl)-4-piperidinyl]-2-benzofurancarboxamide.

6. A pharmaceutical composition useful for regulating cardiac arrhythmias comprising a therapeutically effective amount of a compound according to claim 1, together with one or more non-toxic pharmaceutically acceptable carriers.

7. A pharmaceutical composition according to claim 6 wherein said compound is selected from the group consisting of N-[1-[[4-[(methylsulfonyl)amino]phenyl]methyl]-4-piperidinyl]-2-benzofurancarboxamide;

7-[(methylsulfonyl)amino]-N-[1-[[4-[(methylsulfonyl) amino]phenyl]methyl]-4-piperidinyl]-2-benzofurancarboxamide and 7-[(methylsulfonyl)amino]-N-[1-(phenylmethyl)-4-piperidinyl]-2-benzofurancarboxamide.

8. A method of regulating cardiac arrhythmias comprising administering a therapeutically effective dose of a compound of claim 1 to a mammal in need of such treatment.

9. A method according to claim 8 wherein said compound is selected from the group consisting of N-[1-[[4-[(methylsulfonyl)amino]phenyl]methyl]-4piperidinyl]-2-benzofurancarboxamide;

7-[(methylsulfonyl)amino]-N-[1-[[4-[(methylsulfonyl) amino]phenyl]methyl]-4-piperidinyl]-2-benzofurancarboxamide and 7-[(methylsulfonyl)amino]-N-[I-(phenylmethyl)-4-piperidinyl]-2-benzofurancarboxamide.

* * * * *

UNITED STATES PATENT AND TRADEMARK OFFICE
CERTIFICATE OF CORRECTION

PATENT NO. : 5,210,090     Page 1 of 2

DATED    : May 11, 1993

INVENTOR(S) : Desai, et al.

It is certified that error appears in the above-identified patent and that said Letters Patent is hereby corrected as shown below:

Column 1, line 64, reading "unsubstitutd" should read -- unsubstituted --.

Column 2, line 44, reading "therein" should read -- therein. --.

Column 2, line 46, reading "oxygen" should read -- oxygen. --.

Column 3, line 30, reading "tosylate" should read -- tosylate. --.

Column 3, line 34, reading "reagents" should read -- reagents. --.

Column 6, line 19, reading "0.1" should read -- 0.01 --.

Column 7, line 50, reading "(10I.28g) should read -- (101.28g) --.

Columns 15/16, 1st structure of Example 28, reading the formula

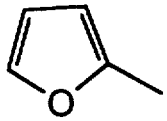     should read     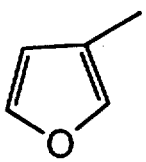

UNITED STATES PATENT AND TRADEMARK OFFICE
CERTIFICATE OF CORRECTION

PATENT NO. : 5,210,090

DATED : May 11, 1993

INVENTOR(S) : Desai, et al.

It is certified that error appears in the above-identified patent and that said Letters Patent is hereby corrected as shown below:

Column 33, line 34, reading "IN potassium" should read -- 1N potassium --.

Column 36, line 63, reading "-N-[I-" should read -- -N-[1- --.

Signed and Sealed this

Twelfth Day of July, 1994

Attest:

BRUCE LEHMAN

Attesting Officer     Commissioner of Patents and Trademarks